United States Patent
Puskas et al.

(10) Patent No.: US 9,480,755 B2
(45) Date of Patent: Nov. 1, 2016

(54) PHARMACEUTICAL COMPOSITION COMPRISING DAPAGLIFLOZIN AND CYCLODEXTRIN

(75) Inventors: István Puskas, Szada (HU); Lajos Szente, Budapest (HU)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 14/117,167

(22) PCT Filed: Jun. 1, 2012

(86) PCT No.: PCT/EP2012/002345
§ 371 (c)(1),
(2), (4) Date: May 15, 2014

(87) PCT Pub. No.: WO2012/163546
PCT Pub. Date: Dec. 6, 2012

(65) Prior Publication Data
US 2014/0249098 A1     Sep. 4, 2014

(30) Foreign Application Priority Data

Jun. 3, 2011 (EP) .................................. 11004534
Aug. 2, 2011 (EP) .................................. 11006361

(51) Int. Cl.
*A61K 47/48* (2006.01)
*A61K 31/7034* (2006.01)
*A61K 31/70* (2006.01)
*A61K 9/20* (2006.01)
*B82Y 5/00* (2011.01)

(52) U.S. Cl.
CPC ......... *A61K 47/4823* (2013.01); *A61K 9/2018* (2013.01); *A61K 9/2054* (2013.01); *A61K 31/70* (2013.01); *A61K 31/7034* (2013.01); *A61K 47/48969* (2013.01); *B82Y 5/00* (2013.01)

(58) Field of Classification Search
CPC .. A61K 31/70; A61K 9/2018; A61K 9/2054; A61K 47/48969; A61K 47/4823; A61K 31/7034
USPC .................... 514/23, 25, 866; 536/1.11, 18.4
See application file for complete search history.

(56) References Cited

U.S. PATENT DOCUMENTS

| 4,555,504 | A | * | 11/1985 | Jones ............................... 514/26 |
| 5,079,237 | A | * | 1/1992 | Husu et al. ...................... 514/58 |
| 5,134,127 | A | * | 7/1992 | Stella et al. ..................... 514/58 |
| 6,515,117 | B2 | * | 2/2003 | Ellsworth et al. ........... 536/17.2 |

FOREIGN PATENT DOCUMENTS

| WO | WO 2010/150219 A1 * | 12/2010 | ............... A61K 9/14 |
| WO | WO 2011/051864 A1 * | 5/2011 | ........... C07D 493/08 |

OTHER PUBLICATIONS

Stern, W.C., Drug News & Perspectives, 1989, 2, 410-415.*

* cited by examiner

*Primary Examiner* — Ganapathy Krishnan
(74) *Attorney, Agent, or Firm* — Milstein Zhang & Wu LLC

(57) ABSTRACT

The present invention relates to pharmaceutical compositions comprising dapagliflozin and cyclodextrin, preferably (2-hydroxy)propyl-b-cyclodextrin or γ-cyclodextrin, preferably as inclusion complex. The invention further relates to a process for producing said pharmaceutical compositions. Finally, the invention relates to the use of cyclodextrin for producing dapagliflozin-containing dosage forms and to methods of purification of dapagliflozin.

18 Claims, 4 Drawing Sheets

Figure 1: in vitro solubility profile
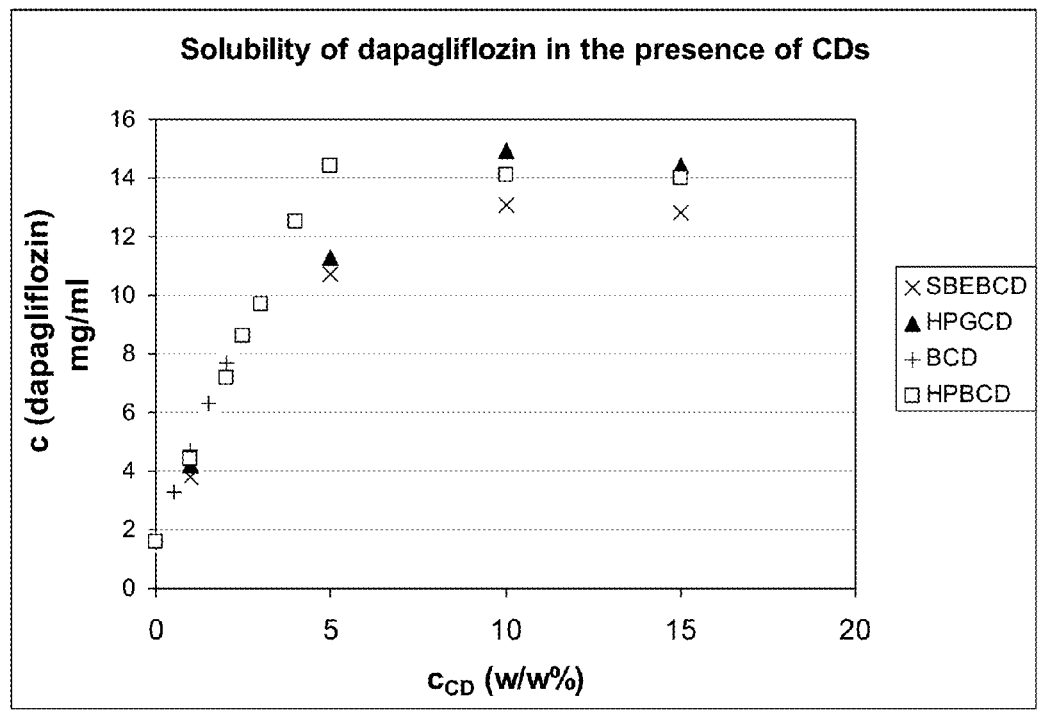

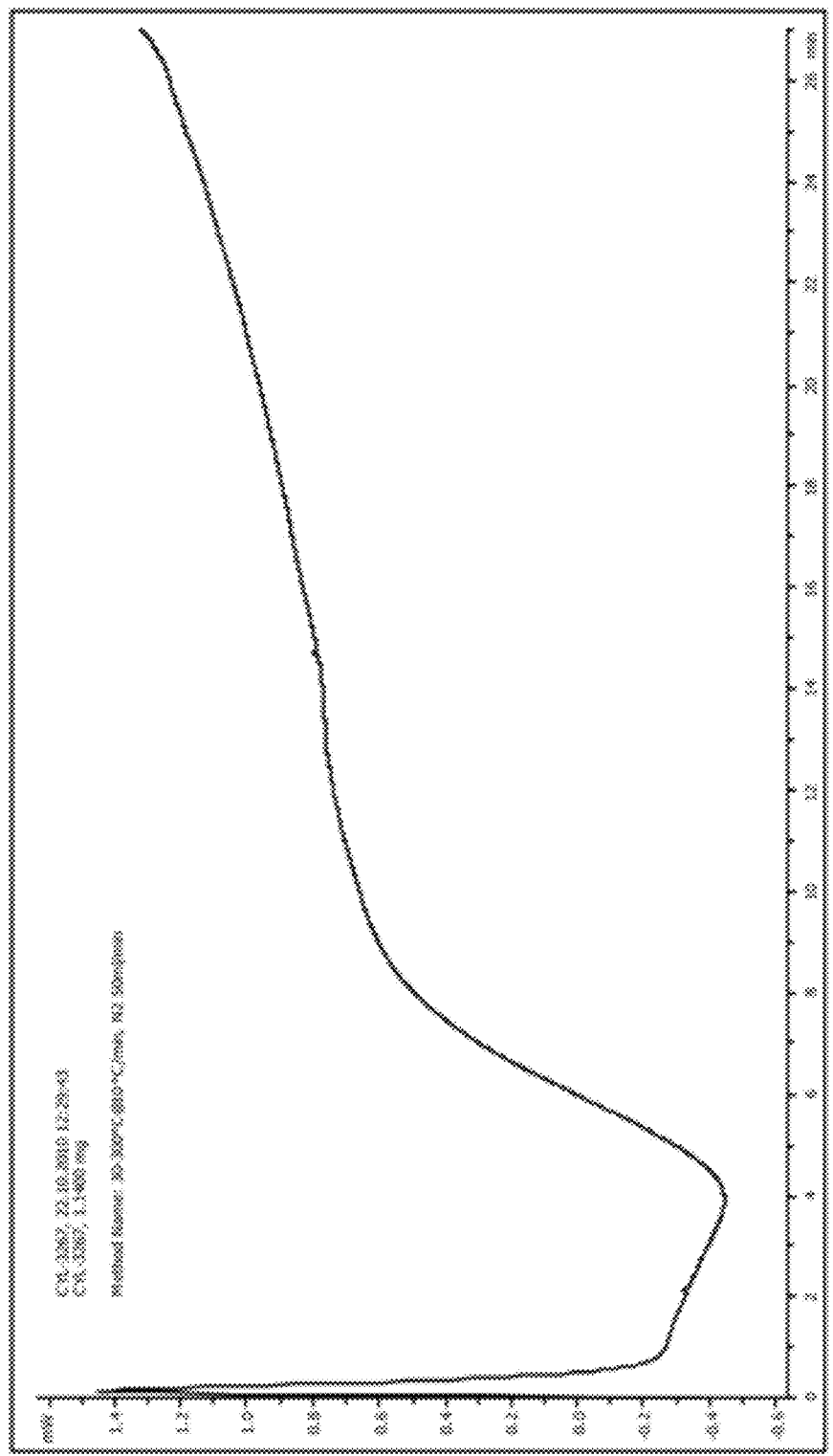
Figure 2: DSC-thermogram of dapagliflozin-cyclodextrin according to Example 1

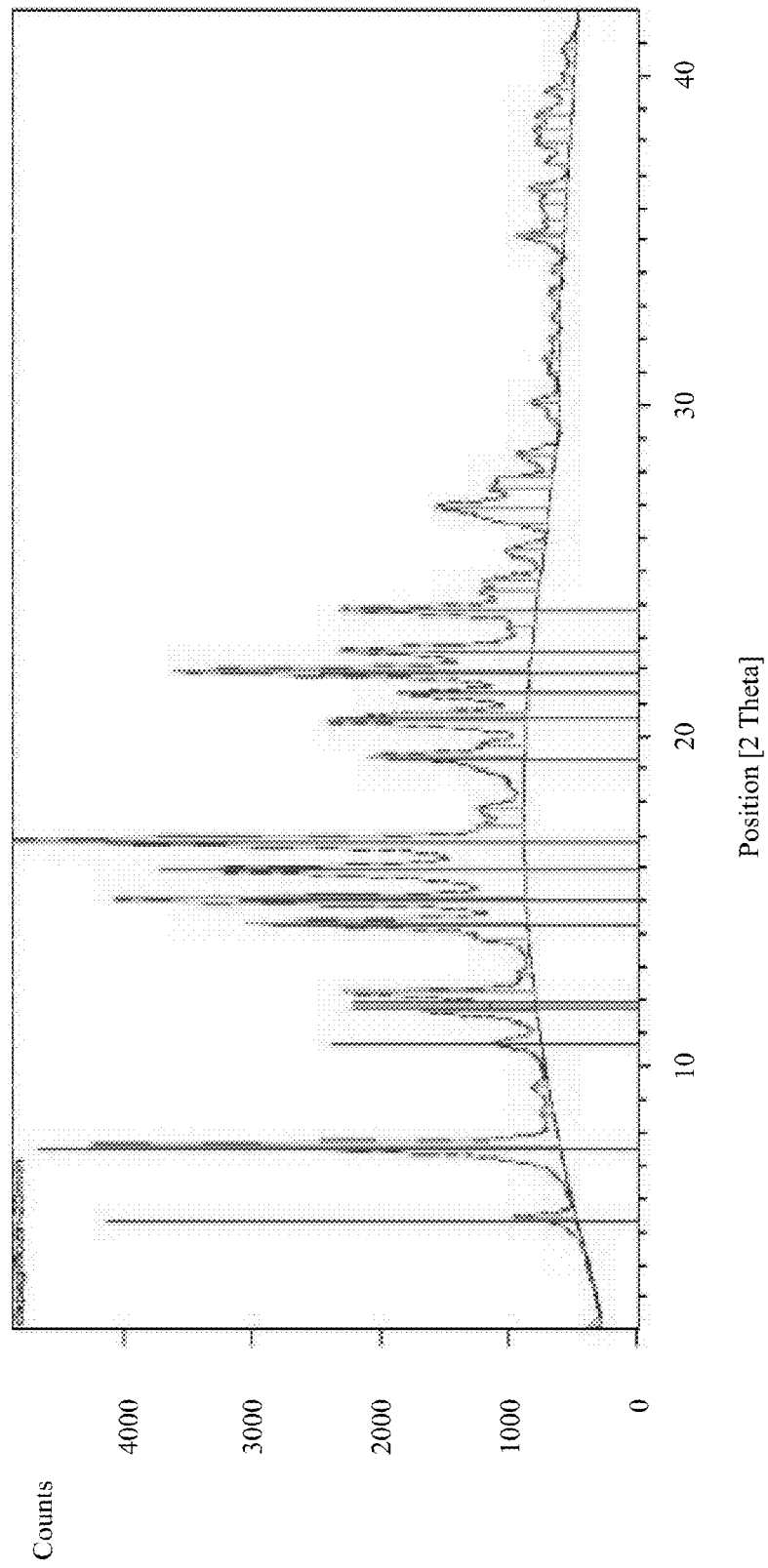
Figure 3: X-ray diffractogram of dapagliflozin/γ-cyclodextrin complex according to Example 5

Figure 4: Dissolution profile of dapagliflozin samples according to Example 6
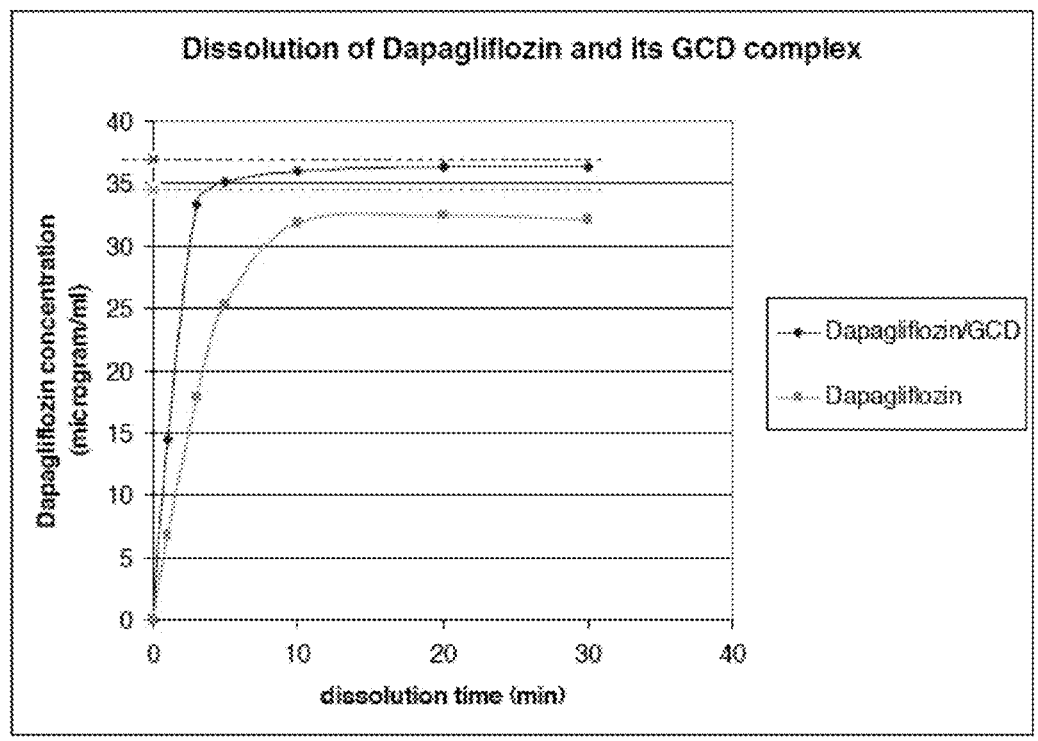

PHARMACEUTICAL COMPOSITION COMPRISING DAPAGLIFLOZIN AND CYCLODEXTRIN

BACKGROUND OF THE INVENTION

The present invention relates to pharmaceutical compositions comprising dapagliflozin and cyclodextrin, preferably as inclusion complexes, further preferably to molecularly dispersed dapagliflozin, comprising cyclodextrin, preferably (2-hydroxy)propyl-b-cyclodextrin or γ-cyclodextrin, and dapagliflozin. The invention further relates to a process for producing said pharmaceutical compositions and to dosage forms comprising said pharmaceutical compositions.

"Dapagliflozin" is reported to be the INN name of the C-aryl glucoside compound (2S,3R,4R,5S,6R)-2-[4-chloro-3-(4-ethoxybenzyl)phenyl]-6-(hydroxymethyl)-tetrahydro-2H-pyran-3,4,5-triol and can be characterized by the following chemical formula:

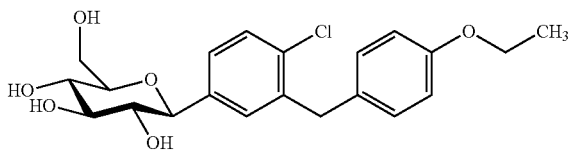

Dapagliflozin is reported to inhibit subtype 2 of the sodium-glucose transport proteins (SGLT2), which is responsible for at least 90% of the glucose reabsorption in the kidney. Blocking this transporter causes blood glucose to be eliminated through the urine. In particular, dapagliflozin is indicated for the treatment for type 1 and type 2 diabetes, in particular, type 2 diabetes.

Dapagliflozin and its synthesis are described in EP 1 506 211 B1. WO 2004/063209 A2 is directed to a process for preparing dapagliflozin and intermediates.

In the art, several dapagliflozin formulations are known. EP 1 506 211 B1 mentions combinations of dapagliflozin with an antidiabetic agent other than SGLT2 inhibitor, an agent for treating the complications of diabetes, an anti-obesity agent, an anti-hypertensive agent, an anti-platelet agent, an anti-atherosclerotic agent, and/or a lipid-lowering agent.

WO 2008/116179 A1 seems to disclose an immediate release formulation comprising dapagliflozin and propylene glycol hydrate.

WO 2008/116195 A2 refers to the use of an SLGT2 inhibitor in the treatment of obesity, wherein the amount of said SGLT2 inhibitor is below the effective amount for treating diabetes.

The micronization of dapagliflozin, however, involves some disadvantages. Firstly, the micronization in the active ingredient results in an undesired low flowability. Furthermore, the micronized active ingredient is more difficult to be compressed and occasionally irregular distribution of the active ingredient can occur within the pharmaceutical formulation to be compressed. Caused by the large extension of the surface during micronization, the tendency of the active ingredient to oxidate increases. Moreover, dapagliflozin when provided in crystalline form is hygroscopic. Thus, it tends to attract water molecules from the surrounding environment through absorption, which leads to diffluence of the active substance, thereby impairing processing abilities and storage stability.

Hence, it was an object of the present invention to overcome the drawbacks of the above-mentioned formulations.

In particular, dapagliflozin should be provided in a form having superior solubility and processing abilities. Preferably, dapagliflozin should be provided in a form, which is highly soluble. In addition, dapagliflozin should be provided in a form, which allows oral application independently from meals. The increase in solubility and permeability should particularly be achieved without a micronization step and preferably without the use of excipients or co-solvents. Moreover, dapagliflozin should be provided in a non-hygroscopic form.

Furthermore, it was an object of the invention to provide dapagliflozin in a form having superior storage properties. Preferably, storage stability for 12 months at 40° C. and 75% humidity should be achieved. After storage under said conditions, impurities should be less than 2 wt.-%, more preferably less than 1 wt.-%.

Particularly, the above-mentioned objects should be solved simultaneously, that means, dapagliflozin should be provided in a non-hygroscopic form having high solubility, high permeability and showing high storage stability.

SUMMARY OF THE INVENTION

The objects of the present invention can be solved by pharmaceutical compositions comprising dapagliflozin and cyclodextrin, preferably as dapagliflozin cyclodextrin inclusion complex, more preferably as "genuine" dapagliflozin-cyclodextrin inclusion complexes and a method for forming such pharmaceutical compositions. Preferably, said preferred inclusion complex can be regarded as a supramolecular, non-covalent inclusion complex. The preferred "genuine" inclusion complex can lead to a novel solid form of dapagliflozin, preferably to a form of molecular dispersity of dapagliflozin. The complexes can be in a form having amorphous or crystalline structure.

A subject of the present invention thus can be a pharmaceutical composition comprising dapagliflozin and cyclodextrin, preferably as an inclusion complex.

A preferred subject of the present invention can be an inclusion complex comprising (2-hydroxy)propyl-b-cyclodextrin (HPBCD), sulfobutylether-b-cyclodextrin (SBEBCD) and/or (2-hydroxy)-propyl-g-cyclodextrin (HPGCD) and γ-cyclodextrin, in particular (2-hydroxy)propyl-b-cyclodextrin (HPBCD) and dapagliflozin, especially in non-crystalline form. Alternatively, a preferred subject of the present invention is an inclusion complex comprising γ-cyclodextrin and dapagliflocin, in particular in crystalline form.

The above illustrated subjects of the present invention are alternative solutions to the above outlined objects.

Moreover, the present invention can be directed to a process for producing a pharmaceutical composition comprising dapagliflozin and cyclodextrin—preferably in form of an inclusion complex—comprising the steps of
  a) dissolving and/or dispersing cyclodextrin in a solvent;
  b) adding dapagliflozin;
  c) subjecting the mixture resulting from step (b) to a mechanical treatment; and
  d) removing the solvent from the reaction mixture, preferably by freeze-drying, spray-drying or filtration.

In a further embodiment, the present invention can be related to the use of cyclodextrin, preferably (2-hydroxy) propyl-b-cyclodextrin or g-cyclodextrin, for producing a dapagliflozin-containing dosage form.

Finally, the present invention can be directed to the method of purification of dapagliflozin, comprising the steps of
a) dissolving and/or dispersing cyclodextrin in a solvent;
b) adding crude dapagliflozin;
c) separating the complexed dapagliflozin from non-complexed residues.

BRIEF DESCRIPTION OF THE DRAWINGS

FIG. 1 shows an in vitro solubility profile.
FIG. 2 shows a DSC-thermogram of dapagliflozin-cyclodextrin according to Example 1.
FIG. 3 shows an X-ray diffractogram of dapagliflozin/γ-cyclodextrin complex according to Example 5.
FIG. 4 shows a dissolution profile of dapagliflozin samples according to Example 6.

DETAILED DESCRIPTION OF THE INVENTION

The term " dapagliflozin " as used in the present application refers to dapagliflozin in free form as well as to its pharmaceutically acceptable solvates, hydrates, enantiomers, polymorphs or mixtures thereof. Dapagliflozin can be further provided as hydrates or solvates, for example propylene glycol hydrate (PGS). Preferably, dapagliflozin can be used in the non-solvated form.

In a particularly preferred embodiment the pharmaceutical composition of the present invention comprises dapagliflozin as the sole pharmaceutical active agent. In an alternative embodiment the pharmceutical composition can comprise dapagliflozin in combination with further pharmaceutical active agent(s).

In a preferred embodiment of the invention, the present invention can refer to a "genuine" dapagliflozin-cyclodextrin inclusion complex. The term "genuine" indicates that the entire and complete amount of dapagliflozin can be entrapped intercalated into the molecular cavities of the cyclodextrin, i.e. dapagliflozin is only present in intercalated form. No adsorbed, un-entrapped crystalline or amorphous dapagliflozin occurs.

Preferably, the inclusion complexes of the present invention can be non-covalent inclusion complexes. Furthermore, the inclusion complexes of the present invention can be supramolecular inclusion complexes. In particular, the inclusion complexes of the present invention can be non-covalent and supramolecular inclusion complexes. The term "supramolecular" is understood as describing self-organizing molecular interactions that result in the formation of new structures that stay together without establishing a covalent linkage.

Generally, in the pharmaceutical composition of the present invention, preferably in the dapagliflozin-cyclodextrin inclusion complexes, the molar ratio of cyclodextrin to dapagliflozin is from 0.5:1 to 2:1, more preferably from 0.8:1 to 1.2:1, most preferably 1.0:1.0. Thus, it is particularly preferred that the dapagliflozin functions as "monofunctional guest" within the cyclodextrin cavity.

The term "cyclodextrin" generally refers to non-reducing cyclic saccharides. Preferably, said cyclic saccharides comprise six, seven or eight glucose units linked by alpha-1,4 interglycosidic bonds. In the present invention cyclodextrins comprising seven glucopyranose units (cycloheptaamylose) are preferred.

The cyclodextrin can be a naturally occurring cyclodextrin or a chemically modified cyclodextrin. Preferably, the cyclodextrin is selected from α-cyclodextrin (ACD), β-cyclodextrin (BCD), 2-hydroxypropyl-β-cyclodextrin (HPBCD), randomly methylated β-cyclodextrin, sulfobutyl ether-β-cyclodextrin (SBEBCD), γ-cyclodextrin and 2-hydroxy-propyl-γ-cyclodextrin (HPGCD).

Furthermore, it is particularly preferred that in all embodiments of the present invention cyclodextrins can be used in the form of cyclodextrin hydrate, particularly (2-hydroxy) propyl-b-cyclodextrin, sulfobutylether-b-cyclodextrin, γ-cyclodextrin and/or (2-hydroxy)-propyl-g-cyclodextrin, most preferably (2-hydroxy)propyl-b-cyclodextrin and γ-cyclodextrin can be used in the form of the hydrate, such as (2-hydroxy)propyl-b-cyclodextrin hydrate. In a preferred embodiment the water content of the cyclodextrin used for making the inclusion complex can be less than 15 wt.-%, preferably 1 to 12 wt.-%, most preferably 1 to 8 wt.-%, based on the total weight of the cyclodextrin.

The cyclodextrins of the present invention can be (partially) substituted. Substitution can be achieved with acetyl groups, alkoxy groups such as carboxymethyl, heteroaromatic or aromatic groups such as benzyl, heteroalkyl or alkyl groups, preferably $C_1$-$C_8$ alkyl groups such as methyl, ethyl, propyl, butyl and pentyl, or with hydroxyalkyl groups such as hydroxyethyl and hydroxypropyl. Preferably, the cyclodextrins can be (partially) substituted with hydroxypropyl groups.

The average degree of substitution is usually 0.1 to 3, preferably 0.3 to 2, more preferably 0.4 to 1.5 and most preferably 0.5 to 1 per glucose unit. In case (2-hydroxy) propyl-b-cyclodextrin can be used, the degree of substitution is 0.1 to 2, preferably 0.3 to 1.5 and most preferably 0.5 to 1 of hydroxypropyl groups per glucose unit.

In an alternative preferred embodiment, the pharmaceutical composition of the invention, preferably the dapagliflozin-cyclodextrin inclusion complex, comprises dapagliflozin and sulfobutylether-b-cyclodextrin, γ-cyclodextrin and/or (2-hydroxy)propyl-b-cyclodextrin.

Generally, the pharmaceutical composition of the present invention, preferably the "genuine" dapagliflozin-cyclodextrin inclusion complex can be achieved if (2-hydroxy) propyl-b-cyclodextrin or γ-cyclodextrin is used.

(2-hydroxy)propyl-b-cyclodextrin is a ring-shaped molecule made up of seven glucose units linked by alpha-1,4 bonds, wherein the glucose units can be (partially) substituted with hydroxypropyl groups.

Furthermore, it is preferred that (2-hydroxy)propyl-b-cyclodextrin (HPBCD) is used in the form of a hydrate, wherein each molecule of (2-hydroxy)propyl-b-cyclodextrin comprises between 12 and 14 molecules of water. In addition, crystalline (2-hydroxy)propyl-b-cyclodextrin, having a monoclinic space group, is used.

γ-Cyclodextrin is a ring-shaped molecule made up of eight glucose units, linked by alpha-1,4 bonds.

The term "γ-cyclodextrin" preferably refers to a "non-substituted form" (as shown in the above formula). This means, the γ-cyclodextrin preferably is not chemically modified e.g. neither alkylated nor hydroxyl-alkylated. Moreover, preferably gamma-cyclodextrin with a bulk density of from 400 to 700 milligram/cm$^3$ is used.

Furthermore, as mentioned above, the γ-cyclodextrin is preferably used in form of a crystalline hydrate. Generally, γ-cyclodextrins can exist in two main classes of crystal structures, namely the cage and tubular (or columnar) structure. The cage structure is often called "HERRING BONE arrangement". In the tubular structure, γ-cyclodextrin monomers stick to each other on their top, forming a cylindrical multi-molecular channel, where e.g. slim but long molecules (e.g. linear polymers) could fit in and form a stable complex. In the present invention it is preferred that γ-cyclodextrin with a cage structure is used.

Furthermore, it is preferred that γ-cyclodextrin is used in the form of a hydrate, wherein each molecule of gamma-cyclodextrin comprises between 12 and 14 molecules of water. In addition, crystalline gamma-cyclodextrin with a monoclinic space group is used.

Generally, cyclodextrins form an inner cavity. Within this application said cavity can be referred to as "nanocavity".

The "genuine" dapagliflozin-cyclodextrin inclusion complex of the present invention can be characterized by the complete inclusion of the dapagliflozin molecule into the nanocavity of the cyclodextrin(s). The completeness of the inclusion process can be monitored via solid state Raman microscopy/spectroscopy and/or by the SEM-ESD electron-microscopic surface mapping.

The preferred "genuine" dapagliflozin-cyclodextrin inclusion complexes of the present invention can be characterized by the complete inclusion of the dapagliflozin into the cavity of the cyclodextrin. The term "complete inclusion" means that the molecular entrapment of dapagliflozin is essentially quantitative. In other words, preferably no surface-bound, adsorbed fraction of the dapagliflozin will occur in the dapagliflozin/cyclodextrin, particularly in the preferred dapagliflozin/β-cyclodextrin and dapagliflozin/γ-cyclodextrin complexes according to the present invention.

Hence, in a preferred embodiment of the invention the pharmaceutical composition comprising dapagliflozin and cyclodextrin preferably can form a solid phase being essentially free of crystalline dapagliflozin. The term "essentially" free means that the preferred inclusion complexes of the present invention do not contain significant amounts of crystalline dapagliflozin bound to the surface of complex particles. Preferably, the pharmaceutical composition of the present can comprise less than 5 wt.-%, more preferably less than 2 wt.-%, more preferably less than 0.5 wt-% dapagliflozin in crystalline, based on the total weight of the pharmaceutical composition.

In a preferred embodiment the residual water content of the preferred dapagliflozin-cyclodextrin inclusion complexes of the present invention is 0.01 to 8 wt. %, more preferably 0.1 to 7.5 wt. %, still more preferably 0.3 to 7.0 wt. %, most preferably 0.5 to 6.5 wt. %, based on the total weight of the complex. Preferably, the water content of the preferred dapagliflozin-cyclodextrin complexes of the present invention does not increase by more than 6 wt. % (in particular, not more than by 3 wt. %) during a storage period of 3 months, at a temperature of 25° C. and a humidity of 60%.

The residual water content is determined according to the Karl Fischer method. For the titration a Mettler Toledo DL—31 titrator is used and the calculation of the water content is performed by the apparatus itself. Usually, a sample of about 50 mg of dapagliflozin cyclodextrin complex is analyzed.

The average particle size of the dapagliflozin-cyclodextrin inclusion complexes, preferably of the (2-hydroxy) propyl-b-cyclodextrin and γ-cyclodextrin dapagliflozin inclusion complexes, is usually between 2 and 20 micrometers, preferably between 5 to 15 micrometers and particularly between 6 and 12 micrometers.

The term "average particle size" refers to the volume average particle size ($D_{50}$), which can be determined by the light scattering method, using a Mastersizer 2000 apparatus, made by Malvern Instruments (wet measurement, 2000 rpm, ultrasonic waves for 60 sec., data interpretation via Fraunhofer method).

Furthermore, the pharmaceutical composition of the present invention—preferably in form of the inclusion complex—can be provided in a solid, particulate form having a bulk density of 450 to 900 mg/cm$^3$, more preferably from 500 to 880 mg/cm$^3$.

The dapagliflozin-cyclodextrin inclusion complexes of the present invention can be regarded as a novel glassy-amorphous solid phase of dapagliflozin. The glassy-amorphous solid phase of dapagliflozin, re-wetted in an aqueous system, preferably can show some liquid crystalline properties that remind of the lyotropic liquid crystalline material. In contrast, the bulk solid was found to have an amorphous structure and is preferably entirely amorphous. Thus, the bulk solid of the dapagliflozin inclusion complex is preferably more than 98 wt. %, more preferably more than 99 wt. % amorphous, most preferably more than 99.5 wt. % amorphous.

In an additional aspect of the present invention, the invention relates to dapagliflozin/cyclodextrin complexes having a substantially crystalline structure. That means that more than 90%, preferably more than 95%, especially more than 99% of the dapagliflozin/cyclodextrin complexes are present in crystalline form.

The present invention further relates to a process for producing a pharmaceutical composition comprising dapagliflozin and cyclodextrin, preferably as "genuine" non-covalent dapagliflozin-cyclodextrin inclusion complex. Hence, a further subject of the present invention can be a process for producing a pharmaceutical composition comprising dapagliflozin and cyclodextrin—preferably in form of an inclusion complex—comprising the steps of a) dissolving or dispersing cyclodextrin in a solvent;
b) adding dapagliflozin;
c) subjecting the mixture resulting from step (b) to a mechanical treatment; and
d) removing the solvent from the reaction mixture, preferably by freeze-drying, spray-drying or filtration.

Generally, the comments made above for dapagliflozin and cyclodextrin can also apply to the process of the present invention. Thus, for example, preferably b-cyclodextrin can be used, particularly (2-hydroxy)propyl-b-cyclodextrin (particularly having the above illustrated water content) can be used in the process of the present invention. Alternatively, γ-cyclodextrin can be used in the process of the present invention.

In step a) of the process of the invention cyclodextrin can be dissolved or dispersed in a suitable solvent. The solvent may be water or an organic solvent, preferably an alcohol, for example ethanol. Furthermore, the solvent may also be a mixture of alcohol and water, wherein the mixing ratio alcohol:water is for example 1:10 to 2:1. In a particularly preferred embodiment the solvent can be deionized water.

The term "dissolving or dispersing" means that cyclodextrin is brought into contact with the solvent, preferably with the water, wherein the solvent wets the surface of the cyclodextrin or the cyclodextrin can be dispersed (i.e. suspended and optionally partially dissolved) in the solvent or, in a preferred embodiment, the cyclodextrin can be completely dissolved in the solvent.

The weight ratio of cyclodextrin:solvent can range from 1:10 to 10:1, preferably from 1:1 to 1:5.

Optionally, the cyclodextrins can be stirred during the dissolving or dispersing step, preferably at a stirring speed from 300 to 450 rpm (rotation per minute).

In an optional but preferred embodiment, dapagliflozin can be subjected to a grinding step (referred to as step (aa)). The grinding step (aa) can lead to a kind of "activation" of the dapagliflozin. Usually, grinding can be carried out for 1 to 30 minutes, preferably for 2 to 10 minutes. Grinding in step (aa) may be carried out in known milling devices, for example a ball mill.

Optionally, dapagliflozin can be (partially or completely) dissolved in a co-solvent (referred to as step (ab))

In step b) of the process dapagliflozin can be added, preferably in particulate form. More preferably, dapagliflozin can be added in crystalline solvated form to the solution of step a). The molar ratio of cyclodextrin to dapagliflozin can be preferably from 1:1 to 5:1, more preferably from 1:1 to 4:1, particularly from 1:1 to 3:1.

Optionally, the mixture of step b) can be stirred, preferably at a stirring speed from 300 to 450 rpm. Stirring may be carried out for 1 to 10 minutes.

In step c) the mixture resulting from step b) can be subjected to a mechanical treatment.

Generally, any mechanical treatment can be suitable to enable the inclusion of the dapagliflozin into the nanocavity. Preferably, the mechanical treatment step can comprise ultrasonic treatment, optionally combined with stirring. Alternatively, but also preferred, mechanical treatment can be carried out by grinding, preferably by co-grinding wetted and/or dispersed cyclodextrin with dapagliflozin.

Generally, ultrasonic treatment can be carried out by immersing the mixture resulting from step b) into an ultrasonic device, for example, an ultrasonic bath. Examples of ultrasonic-treatment are hydrodynamic cavitation, sonofragmentation and/or sono-cavitation or co-grinding. For example, ultrasonic treatment can be carried out with Tesla ultrasonic equipment.

Ultrasonic treatment can preferably be performed by using ultrasonic waves having a frequency of 5 to 100 kHz, more preferably of 10 to 80 kHz. Furthermore, ultrasonic treatment is preferably performed by using ultrasonic waves having an intensity of 50 to 5000 W, more preferably 500 to 1000 W. As an example, 1000 W and 20 kHz or 500 W and 58 kHz can be used.

This means that instead of the relatively long 6-8 hours stirring time for reaching complete inclusion, which is used traditionally in the art for complexation, the stirring time can significantly be reduced by the above-mentioned sonofragmentation or sono-cavitation process. By this high-energy ultrasonic treatment, the inclusion complexation technology can become more efficient and economic.

In addition to the ultrasonic treatment (for example hydrodynamic cavitation, sono-fragmentation or sonocavitation), the reaction mixture may be agitated (for example using traditional propeller stirrer), preferably with a rotation speed of 300-450 rpm (rotation per minute).

As mentioned above, the mechanical treatment step can also be carried out by grinding, preferably by co-grinding dispersed cyclodextrin with dapagliflozin. Generally, grinding can be carried out in known milling devices, for example a ball mill or a pin mill. It is preferred that if the mechanical treatment step c) is carried out by grinding, then the optional step (aa) (=activation of cyclodextrin) is carried out.

Usually, the mechanical treatment can be carried out for 1 to 30 minutes, preferably for 5 to 20 minutes. Furthermore, mechanical treatment can be carried out at a temperature from 5 to 50° C., preferably at room temperature (about 20° C.).

Once solid phase transformation (occurring in step c)) is completed, the solvent of the reaction mixture can be removed in step d).

Generally, the methods known in the art for removing solvents are suitable. Preferably, the solvent can be removed by freeze-drying or spray-drying. The removal of the solvent by a spray-drying step is particularly preferred. Alternatively, removing the solvent by filtration is particularly preferred.

Generally, spray-drying can be carried out, using an inlet temperature of 150 to 200° C., preferably about 180° C., and an outlet temperature of about 80 to 100° C., preferably of about 95° C. For example, spray-drying can be carried out by using a Büchi® Lab Niro spray-drier.

After removing the water, the pharmaceutical compositions of the present invention, preferably the dapagliflozin-cyclodextrin inclusion complexes, can be rewetted, dispersed or dissolved. The fastest dissolving form of the dapagliflozin inclusion complexes of the present invention usually can be achieved, if in step d) the solvent is removed by freeze-drying (liophilisation) the inclusion complex.

Steps a) to c) can be carried out subsequently or simultaneously. In a preferred embodiment steps a), b) and c) can be carried out subsequently.

Generally, the process of the present invention is suitable for preparing the inclusion complexes of the present invention, preferably achieving a yield of from 80 to 99%, more preferably from 90 to 98%.

In a preferred embodiment of the process of the invention the pharmaceutical composition comprising dapagliflozin and cyclodextrin can be formed in the absence of excipients and/or co-solvents.

Further subjects of the present invention can be pharmaceutical compositions, preferably as inclusion complexes, obtainable by the above-mentioned process.

The pharmaceutical compositions of the present invention, preferably as inclusion complexes can be applied in the form of a dosage form.

Hence, a further subject of the present invention is a dosage form comprising a pharmaceutical composition according to the present invention and optionally one or more pharmaceutical excipients.

In the dosage form of the present invention one or more pharmaceutically acceptable excipient(s), such as fillers, binding agents, lubricants, glidants, surfactants and disintegrating agents can be employed. Regarding the above-mentioned pharmaceutically acceptable excipients, the application refers to "Lexikon der Hilfsstoffe für Pharmazie, Kosmetik and angrenzende Gebiete", edited by H. P. Fiedler, $4^{th}$ Edition, Edito Cantor, Aulendorf and earlier editions, and "Hand-book of Pharmaceutical Excipients", Third Edition, edited by Arthur H. Kibbe, American Pharmaceutical Association, Washington, USA, and Pharmaceutical Press, London.

Alternatively the pharmaceutical excipients are described in the European Pharmacopoeia (Ph.Eur.) and/or in the US Pharmacopoeia (USP).

Fillers can be used to increase the bulk volume and weight of a low-dose drug to a limit at which a dosage form can be formed. Fillers may fulfill several requirements, such as being chemically inert, non-hygroscopic, biocompatible, easily processable and may possess good biopharmaceutical properties. Examples of fillers are lactose, sucrose, glucose, mannitol, calcium carbonate, cellulose and others.

The fillers can be present in the dosage form of the present invention in an amount of 0 to 70 wt. %, preferably 10 to 68 wt. %, more preferably 15 to 65 wt. % and still more preferably 25 to 60 wt. % based on the total weight of the dosage form.

In a preferred embodiment of the present dosage form the excipient can be a binding agent. Binding agents usually are regarded as substances for ensuring that the composition can be formed with the required mechanical strength, preferably when compressing to a tablet.

The binding agent can be present in an amount of 0 to 30 wt. %, preferably 1 to 25 wt. %, more preferably 5 to 20 wt. % and still more preferably 7 to 15 wt. % based on the total weight of the dosage form. In a preferred embodiment the present dosage form does not comprise a binding agent.

The binding agent for the preparation of the dosage form is preferably a polymer. The polymer that can be used for the preparation of the dosage form preferably has a glass transition temperature (Tg) of more than 18° C., more preferably 30° C. to 150° C., especially preferred 40° C. to 100° C. In the context of this invention the glass transition temperature is determined by means of dynamic differential scanning calorimetry (DSC). For this purpose a Mettler Toledo DSC 1 apparatus can be used. The work is performed at a heating rate of 1-20° C./min., preferably 5-15° C./min., and at a cooling rate of 5-25° C., preferably 10-20° C./min.

The dosage form of the invention may, for example, comprise the following hydrophilic polymers as binding agent: polyvinyl pyrrolidone, polyvinyl acetate (PVAC), polyvinyl alcohol (PVA), vinyl pyrrolidone/vinyl acetate copolymers (such as Kollidon® VA64), polyalkylene glycols, such as polypropylene glycol or preferably polyethylene glycol, block copolymers of polyethylene glycol, especially block copolymers of polyethylene glycol and polypropylene glycol (Pluronic®, BASF), disaccharides, such as lactose, and mixtures of thereof.

Lubricants are generally used in order to reduce sliding friction. In particular, the intention is to reduce the sliding friction found during tablet pressing between the punch moving up and down in the die and the die wall on the one hand, and between the edge of the tablet and the die wall on the other hand. Suitable lubricants are, for example, stearic acid, adipic acid, sodium stearyl fumarate and/or magnesium stearate.

Lubricants are generally used in an amount of up to 3 wt. %, preferably 0.1 to 2 wt. % based on the total weight of the dosage form.

Glidants can be used to improve the flowability. For example, talc can be used as glidant. More preferably, colloidal silica (for example Aerosil®) is used. Preferably, the glidant can be present in an amount of up to 3 wt. %, in particular, 0.1 to 2 wt. %, based on total weight of the dosage form. Preferably, the silica has a specific surface area of 50 to 400 m2/g, measured by gas adsorption according to Ph. Eur., 6.0, Chapter 2.9.26.

Surfactants usually are substances which lower the interfacial tension between two phases thus enabling or supporting the formation of dispersions or working as a solubilizer. Common surfactants can be alkyl sulfates (for example sodium lauryl sulfate), alkyltrimethylammonium salts, alcohol ethoxylates, sorbitanes and the like.

The surfactant can be present in the dosage form of the present invention in an amount of 0 to 10 wt. %, preferably 0.1 to 8 wt. %, more preferably 0.3 to 5 wt. % and still more preferably 0.7 to 3.0 wt. % based on the total weight of the dosage form.

Disintegrants usually are compounds which can enhance the ability of the dosage form to break into smaller fragments when in contact with a liquid, preferably water. Preferred disintegrants are sodium carboxymethyl starch, cross-linked polyvinylpyrrolidone (Crospovidone), sodium carboxymethyl glycolate (for example Explotab®), swelling polysaccharide, for example soy polysaccharide, carrageenan, agar, pectin, starch and derivates thereof, protein, for example formaldehyde-casein, sodium bicarbonate or mixtures thereof.

The disintegrant can be present in the dosage form of the present invention in an amount of 0 to 20 wt. %, preferably 1 to 17 wt. %, more preferably 3 to 15 wt. % and still more preferably 7 to 12 wt. % based on the total weight of the dosage form.

A pharmaceutical excipient can preferably perform more than one function in a pharmaceutical formulation, for example lactose may be used as filler as well as binding agent.

In an alternative preferred embodiment, in order to provide an unambiguous delimitation, the fiction will preferably apply that a substance which is used as a particular excipient is not simultaneously also used as a further pharmaceutical excipient. For example, microcrystalline cellulose—if used as filler—is not additionally used as disintegrant (even though microcrystalline cellulose also exhibits a certain disintegrating effect).

Generally, the comments given above on preferred embodiments of pharmaceutical compositions of the present invention can also apply for the dosage form of the present invention. In particular, the dosage forms of the present invention can be essentially free of crystalline dapagliflozin. The term "essentially" free means that the dosage forms of the present invention do not contain significant amounts of crystalline dapagliflozin. Preferably, the dosage forms of the present invention comprise less than 5 wt.-%, more preferably less than 1 wt.-%, more preferably less than 0.1 wt.-% dapagliflozin in crystalline form, based on the total weight of the dosage form.

In a preferred embodiment of the invention the dosage form is adapted to be administered orally or intravenously. The administration of the present dosage form can preferably be applied independently from meals.

In a preferred embodiment the pharmaceutical composition of the present invention can preferably be used as intermediate or as final dosage form. Preferably, the composition of the present invention is used as intermediate, which is preferably further processed into a dosage form, more preferably into an oral dosage form, most preferably into a solid oral dosage form. The processing into a dosage form can be achieved by means of suitable methods, such as filling into sachets or capsules or by compressing into tablets.

Optionally, before the filling or compression step the composition can be granulated. Direct compression is preferred.

Therefore, the composition of the invention can be employed to prepare a dosage form, more preferably a solid oral dosage form, in particular a capsule or tablet.

In a preferred embodiment of the invention the dosage form can be a tablet.

In a preferred embodiment the dosage form according to the invention provides an immediate release ("IR") of dapagliflozin. This means that the release profile of the dosage forms of the invention according to USP method (paddle, 900 ml, 0.1 n HCl, 75 rpm, 37° C.) after 10 minutes usually indicates a content release of at least 75%, preferably at least 85%, especially at least 90%.

The oral dosage form of the invention may be a tablet which can be swallowed unchewed (non-film-coated or preferably film-coated).

In a preferred embodiment, the tablet of the present invention can be film-coated. For this purpose, methods known in the art for film-coating a tablet may be employed.

Generally, film coatings can be prepared by using cellulose derivatives, poly(meth)acrylate, polyvinyl pyrrolidone, polyvinyl acetate phthalate, and/or shellac or natural rubbers such as carrageenan.

In a preferred embodiment of the present invention the film coating can be a film coating essentially without affecting the release of the active agent.

Preferred examples of film coatings which do not affect the release of the active ingredient can be those including poly(meth)acrylate, methylcellulose (MC), hydroxypropyl methylcellulose (HPMC), hydroxypropyl cellulose (HPC), hydroxyethyl cellulose (HEC), polyvinyl pyrrolidone (PVP) and mixtures thereof.

These polymers can have an average molecular weight of 10,000 to 150,000 g/mol.

The tablet of the invention preferably can have a hardness of 25 o to 250 N, particularly preferably of 30 to 180 N or 40 to 150 N. The hardness is determined in accordance with Ph.Eur., 6.0, Chapter 2.9.8.

In addition, the tablet of the invention preferably can have a friability of less than 3%, more preferably less than 2%, in particular 0.1 to 1.2%. The friability is determined in accordance with Ph.Eur., 6.0, Chapter 2.9.7.

Further, the dosage form, preferably the tablet, of the invention preferably has contents of active agent(s) which lie within the concentration of 90 to 110%, preferably 95 to 105%, especially preferred 98 to 102% of the average content of the active agent(s). This "content uniformity" is determined with a test in accordance with Ph. Eur., 6.0, Chapter 2.9.6. According to that test, the content of the active agents of each individual tablet out of 20 tablets must lie between of 90 to 110%, preferably 95 to 105%, especially 98 to 102% of the average content of the active agent(s). Therefore, the content of the pharmaceutical active agent in each tablet of the invention differs from the average content of the pharmaceutical active agent by at most 10%, preferably by at most 5% and especially by at most 2%.

The above details regarding hardness, friability and content uniformity preferably relate to the non-film-coated tablet.

In a preferred embodiment the dosage form of the present invention can comprise the following amounts of components:

1 to 100 mg dapagliflozin, preferably 2 to 75 mg dapagliflozin, particularly 5 to 50 mg dapagliflozin, 25 to 300 mg cyclodextrin, preferably 40 to 250 mg cyclodextrin, particularly 50 to 150 mg cyclodextrin, 25 to 350 mg filler, preferably 50 to 250 mg filler, particularly 75 to 200 mg filler, 0 to 15 mg glidant, preferably 0.5 to 10 mg glidant, particularly 1 to 5 mg glidant 0 to 15 mg lubricant, preferably 0.5 to 10 mg lubricant, particularly 1 to 5 mg lubricant, 0 to 25 mg disintegrant, preferably 2 to 17 mg disintegrant, particularly 3 to 13 mg disintegrant, 0 to 60 mg binding agent, preferably 3 to 55 mg binding agent, particularly 10 to 50 mg binding agent.

In a preferred embodiment the dosage form of the present invention can comprise:

1 to 20 wt. % dapagliflozin, preferably 3 to 18 wt. % dapagliflozin, particularly 4 to 13 wt. % dapagliflozin, 30 to 45 wt. % cyclodextrin, preferably 25 to 40 wt. % cyclodextrin, particularly 20 to 35 wt. % cyclodextrin, 10 to 68 wt. % filler, preferably 15 to 65 wt. % filler, particularly 25 to 60 wt. % filler, 0.01 to 3 wt. % glidant, preferably 0.1 to 2.5 wt. % glidant, particularly 0.1 to 2 wt. % glidant, 0.01 to 3 wt. % lubricant, preferably 0.1 to 2.5 wt. % lubricant, particularly 0.1 to 2 wt.% lubricant, 1 to 20 wt. % disintegrant, preferably 1.5 to 15 wt. % disintegrant, particularly 2 to 10 wt. % disintegrant, 0 to 30 wt. % binding agent, preferably 0.5 to 20 wt. % binding agent, particularly 2 to 15 wt. % binding agent, based on the total weight of the dosage form.

A further subject of the invention is a method for preparing the dosage form of the present invention comprising the steps of (a1) mixing a pharmaceutical composition comprising cyclodextrin and dapagliflozin and optionally one or more pharmaceutical excipient(s), (a2) optionally granulating the mixture from step (a1), (a3) processing the mixture resulting from step (a1)) or the granulates from step (a2) into a dosage form, and (a4) optionally film-coating the dosage from.

In a preferred embodiment, step (a1)) can be characterized by mixing the pharmaceutical composition and optionally one or more pharmaceutical excipient(s) as outlined above.

The mixing (a1)) can be carried out with conventional mixing devices. In order to ensure an even distribution, mixing in intensive mixers is preferred. Suitable mixing devices can preferably be a compulsory mixer or a free fall mixer, for example a Turbula® T 10B (Bachofen AG, Switzerland). Mixing can be carried out, for example, for 1 minute to 1 hour, preferably for 5 to 30 minutes.

In a preferred embodiment, the mixing (a1)) can be conducted such that the pharmaceutical composition can be mixed with a first part of the optionally one or more excipient(s) in a mixing device, for example in a high shear or tumbler mixer. After this first mixing step a second part of the one or more excipient(s) can be added, which may be followed by a second mixing step. This procedure can be repeated until the last part of the one or more excipient(s) is added, preferably one to five times. This kind of mixing can assure an even distribution of the active agent and provides a mass for further processing in step (a2) or step (a3), for example for a granulation or tableting process.

In step (a2) the mixture from step (a1)) can be optionally granulated. "Granulating" is generally understood to mean the formation of relatively coarse or granular aggregate material as a powder by assembling and/or aggregating finer powder particles (agglomerate formation, or build-up granulation) and/or the formation of finer granules by breaking up coarser aggregates (disintegration, or break-down granulation).

Granulation can conventionally mean wet or dry granulation.

Dry granulation, which is preferred, is generally carried out by using pressure or temperature. In a preferred embodiment of the invention, granulating the mixture from step (a1)) can be performed, for example, by "slugging", using a large heavy-duty rotary press and breaking up the slugs to granulates with a hammer mill or by roller compaction, using for example roller compactors by Powtec or Alexanderwerk. The granulates are then optionally screened.

In step (a3) the mixture resulting from step (a1)) or optionally the granulates from step (a2) can be further processed into a dosage form. For this purpose, said mixture or said granulates can, for example, be filled into sachets or capsules.

In a preferred embodiment, step (a3) can include compressing the mixture resulting from step (a1)) or optionally the granulates from step (a2) and optionally further excipient(s), such as lubricant, into tablets.

The compression of the mixture of step (a1)) can preferably be a direct compression. This direct compression step can preferably be carried out on a rotary press, for example on a Fette® 102i (Fette GmbH, Germany) or a Riva® piccola (Riva, Argentina). If a rotary press is applied, the main compaction force can range from 1 to 50 kN, preferably from 2 to 40 kN, more preferably form 3 to 30 kN.

In an alternative embodiment the granulates from step (a2) can be compressed into tablets.

In step (a4) the tablet can optionally be film-coated.

The preferred embodiments of the dosage form of the present invention are summarized by the following items:

1. Dosage form containing a pharmaceutical composition according to the invention (i.e. dosage form comprising a pharmaceutical composition comprising cyclodextrin and dapagliflozin, preferably in form of an inclusion complex) and optionally one or more pharmaceutical excipient(s).

2. Dosage form according to item 1, forming a solid phase being essentially free of crystalline dapagliflozin.

3. Dosage form according to item 1 or 2, wherein the dosage form is adapted to be administered orally or intravenously 4. Dosage form according to any one of items 1 to 3, wherein the molar ratio of cyclodextrin to dapagliflozin is from 0.5:1 to 2:1, more preferably from 0.8:1 to 1.2:1, most preferably about 1:1.

5. Dosage form according to any one of items 1 to 4, wherein cyclodextrin is (2-hydroxy)propyl-β-cyclodextrin, sulfobutylether-b-cyclodextrin or (2-hydroxy)propyl-γ-cyclodextrin or γ-cyclodextrin, preferably (2-hydroxy)propyl-β-cyclodextrin or γ-cyclodextrin.

6. Dosage form according to any one of items 1 to 5, wherein the dosage form provides an immediate release ("IR") of dapagliflozin, preferably an content release of at least 75% after 10 minutes, determined according to USP method (paddle, 900 ml, 0.1 n HCl, 75 rpm, 37° C.).

7. Dosage form according to any one of item 1 to 6, wherein the dosage form of the present invention comprises the following amounts of components:

1 to 100 mg dapagliflozin, preferably 2 to 75 mg dapagliflozin, particularly 5 to 50 mg dapagliflozin, 25 to 300 mg cyclodextrin, preferably 40 to 250 mg cyclodextrin, particularly 50 to 150 mg cyclodextrin, 25 to 350 mg filler, preferably 50 to 250 mg filler, particularly 75 to 200 mg filler, 0.1 to 15 mg glidant, preferably 0.5 to 10 mg glidant, particularly 1 to 5 mg glidant 0.1 to 15 mg lubricant, preferably 0.5 to 10 mg lubricant, particularly 1 to 5 mg lubricant, 1 to 25 mg disintegrant, preferably 2 to 17 mg disintegrant, particularly 3 to 13 mg disintegrant, 0 to 60 mg binding agent, preferably 3 to 55 mg binding agent, particularly 10 to 50 mg binding agent.

8. Dosage form according to any one of item 7, wherein the dosage form of the present invention comprises:

1 to 20 wt. % dapagliflozin, preferably 3 to 18 wt. % dapagliflozin, particularly 4 to 13 wt. % dapagliflozin, 30 to 45 wt. % cyclodextrin, preferably 25 to 40 wt. % cyclodextrin, particularly 20 to 35 wt. % cyclodextrin, 10 to 68 wt. % filler, preferably 15 to 65 wt. % filler, particularly 25 to 60 wt. % filler, 0.01 to 3 wt. % glidant, preferably 0.1 to 2.5 wt. % glidant, particularly 0.1 to 2 wt. % glidant, 0.01to 3 wt. % lubricant, preferably 0.1 to 2.5 wt. % lubricant, particularly 0.1 to 2 wt. % lubricant, 1 to 20 wt. % disintegrant, preferably 1.5 to 15 wt. % disintegrant, particularly 2 to 10 wt. % disintegrant, 0 to 30 wt. % binding agent, preferably 0.5 to 20 wt. % binding agent, particularly 2 to 15 wt. % binding agent.

9. Dosage form according to any one of items 1 to 8, wherein the dosage form is in form of a tablet.

10. Dosage form according to item 9, wherein the tablet has a hardness of 25 to 250 N, determined in accordance with Ph.Eur., 6.0, Chapter 2.9.8, a friability of less than 3%, determined in accordance with Ph.Eur., 6.0, Chapter 2.9.7., and a content uniformity of 95 to 105%, determined in accordance with Ph. Eur., 6.0, Chapter 2.9.6.

11. Method for preparing a dosage form according to any one of items 1 to 10, wherein the method comprises the steps of (a1) mixing a pharmaceutical composition according to the invention and optionally one ore more pharmaceutical excipient(s), (a2) optionally granulating the mixture from step (a1), (a3) processing the mixture resulting from step (a1) or the granulates from step (a2) into a dosage form, and (a4) optionally film-coating the dosage form.

12. Method according to item 11, wherein the method is a direct compression of the mixture of step (a1).

13. Method according to item 11, wherein the step (a2) of optionally granulating the mixture from (a1) is a dry granulation step, preferably a dry compaction step.

A further subject of the present invention is the use of cyclodextrin, preferably (2-hydroxy)propyl-b-cyclodextrin or γ-cyclodextrin, for producing a dapagliflozin-containing dosage form. For the use of the present invention all explanations given above for dapagliflozin, for cyclodextrin and/or for the dosage form apply analogously.

It was further surprisingly found by the present inventors that, when adding crude dapagliflozin to cyclodextrin, in particular (2-hydroxy)propyl-b-cyclodextrin or γ-cyclodextrin, under conditions that enable the compounds to form the above described dapagliflozin-cyclodextrin complex, a portion of the drug remained uncomplexed, regardless of any further addition of cyclodextrin, water or ultrasonic treatment. Herefrom it may be concluded that only the dapagliflozin can be included in the cavity of the cyclodextrin, but not the impurities of dapagliflozin. The term "crude dapagliflozin" thus can relate to any dapagliflozin, which can contain an impurity, such as any undesired compound. As a consequence, the term "crude" also applies to all kinds of purity grades of dapagliflozin, such as technical grade dapagliflozin.

Thus, the invention can further relate to a method of purification of dapagliflozin, comprising a) dissolving or dispersing cyclodextrin in a solvent;

b) adding crude dapagliflozin;

c) separating the complexed dapagliflozin from non-complexed residues.

Step c) can preferably be achieved by filtration, or any other method for separation known to the skilled person.

In step (c) the solvent can be removed. It is preferred that the solvent is completely removed. In a preferred embodiment the composition of the present invention comprises an amount of residual solvent of 100 to 1000 ppm, more preferably of 150 to 500 ppm, still more preferably of 200 to 400 ppm.

Within this application the amount of the residual solvent in the composition of the present invention is determined via gas chromatography.

Gas chromatographic conditions for residual solvent analysis:

| Instrument | Agilent Gas Chromatograph (6890N) equipped with Gerstel Multi Purpose Sampler MPS2 |
|---|---|
| Column | BP-624, 30M × 0.53 mm, of 3.0 μm |
| Injector | 200° C., Split Ratio 3:1, Total flow: 10.4 ml/min |
| Carrier gas | Nitrogen @ 2.0 ml/min [(constant flow), (Eq. Pressure: 1.45 psi)] |
| Oven | 40° C. (hold for 15 min), Ramp 10° C./min upto 160° C. (hold for 5 min) |
| Detector | FID @ 250° C. |
| Hydrogen | @ 30.0 ml/min |
| Air | @ 300.0 ml/min |
| Make up flow | 28 ml/min |
| Quantity of sample | 100 mg |
| Solvent for dissolving | N,N-Dimethyl formamide |

For the method of purification of dapagliflozin, generally, the steps and the comments given above about preferred embodiments of the method for producing pharmaceutical compositions can be applied.

The subject invention thus further relates to the use of cyclodextrin and, in particular, (2-hydroxy)propyl-b-cyclodextrin or γ-cyclodextrin in a method of purification of dapagliflozin.

A further subject of the present invention is a pharmaceutical composition comprising dapagliflozin, preferably in form of an inclusion complex. In particular, the invention relates to a pharmaceutical composition comprising dapagliflozin characterized in that on introduction to water (at 25° C.) said composition is capable of forming a solution comprised of not less than 5 mg dapagliflozin per ml water. Preferably, the solution comprises 5 mg to 50 mg dapagliflozin, more preferably 6 to 40 mg, still more preferably 8 to 30 mg.

The present invention is illustrated by the following examples.

EXAMPLES

Example 1

Preparation of a Dapagliflozin/(2-hydroxy)propyl-b-cyclodextrin Inclusion Complex using Pure Dapagliflozin 9.03 g HPBCD (8.43 g-6.2 mmol on dry basis, Roquette Frères) were dissolved in 100 ml distilled water. 2.30 g dapagliflozin (5.6 mmol) was added to the solution at 23° C. The solution was stirred for 15 minutes and additional 25 ml of distilled water were added. After treating the solution in an ultrasonic bath for 7 minutes, the resulting clear solution was frozen and freeze-dried in bulk at 72 m Torr (−52°) for 32 hours.

The resulting pharmaceutical composition can be examined by DSC. The differential scanning calometry (DSC) was performed using the following parameters:
Start Temperature: 30° C.
End Temperature: 300° C.
Heating rate: 10° C./min.
Segment gas: Nitrogen
Segment gas glow rate: 50 ml/min.
Sample holder: Aluminum standard 40 μl
Sample quantity: 1-2 mg As derivable from FIG. 2, the DSC-thermogram showed the absence of any crystalline dapagliflozin in the pharmaceutical composition.

Example 2

Preparation of a Dapagliflozin/(2-hydroxy)propyl-b-cyclodextrin Inclusion Complex using Crude Dapagliflozin 9.03 g HPBCD (8.43 g-6.2 mmol on dry basis, Roquette Frères) were dissolved in 100 ml distilled water. 2.30 g (5.6 mmol) crude dapagliflozin were added to the solution at 23° C. The solution was stirred for 15 minutes and additional 25 ml of distilled water were added. After pretreating the solution in an ultrasonic bath for 7 minutes, the heterogeneous liquid was filtered through a cellulose nitrate membrane, having a nomimal pore size of 0.22 μm. The resulting clear solution was frozen and freeze-dried in bulk at 72 m Torr (−52°) for 32 hours.

Example 3

In vitro Solubility Profiles

The effect of cyclodextrins on the aqueous solubility of dapagliflozin was studied in deionised water at 25±2° C. The solubilizing effect was studied by preparing samples having a cyclodextrin concentration in the range of 1 to 15 wt. %. Due to the relatively low solubility of BCD, the study was performed by adding smaller amounts of cyclodextrin (0.5-2 wt. %).

The following cyclodextrins were used:
b-cyclodextrin (BCD): CYL-2518/2 (Wacker Chemie GmbH)
(2-hydroxy)propyl-b-cyclodextrin (HPBCD): E0062 (Roquette Frères)
sulfobutylether-b-cyclodextrin (SBEBCD): 47K040508 (CycloLab)

TABLE 1

Solubility of dapagliflozin in deionised water at 25 ± 2° C. in the presence of different cyclodextrins

| Applied Cyclodextrin | wt. % cyclodextrin | Dissolved Dapagliflozin (mg/ml) |
|---|---|---|
| none | | 1.6 |
| BCD | 0.5 | 3.3 |
| BCD | 1.0 | 4.7 |
| BCD | 1.5 | 6.3 |
| BCD | 2.0 | 7.7 |
| SBEBCD | 1.0 | 3.8 |
| SBEBCD | 5.0 | 10.7 |
| SBEBCD | 10.0 | 13.1 |
| SBEBCD | 15.0 | 12.8 |
| HPGCD | 1.0 | 4.2 |
| HPGCD | 5.0 | 11.3 |
| HPGCD | 10.0 | 14.9 |
| HPGCD | 15.0 | 14.4 |
| HPBCD | 1.0 | 4.4 |
| HPBCD | 2.0 | 7.2 |
| HPBCD | 2.5 | 8.6 |
| HPBCD | 3.0 | 9.7 |
| HPBCD | 4.0 | 12.5 |
| HPBCD | 5.0 | 14.4 |
| HPBCD | 10.0 | 14.1 |
| HPBCD | 15.0 | 14.0 |

The results are plotted in FIG. 1.

The phase solubility studies indicate that the interactions between dapagliflozin and cyclodextrins bring about significant solubility enhancement in deionised water in a cyclodextrin-concentration dependent manner.

Example 4

Third Component Trial

Literal examples indicate that the effectiveness of complex formation may be increased upon the addition of hydroxycarboxylic acids, especially citric acid in case the complex forming cyclodextrin or its complex is subject to aggregation. Often this is the case when parent cyclodextrins are applied. Since the selected cyclodextrin (HPBCD) of adequate quality is not likely to aggregate, the addition of a third component is not required. The solubility isotherms of BCD and HPBCD practically coincide within experimental error, indicating that the outer sphere interactions (responsible for aggregation) have no significant effect on the solubility, for example, mainly the cavity size determines the complex stability parameters. As a proof of concept, representative isotherm data were determined in the presence of citric acid (added in equimolar ratio with the pharmacon) and compared to the original dissolved concentrations (Table 2). The data show that the presence of the hydroxycarboxylic acid does not have a significant effect on the solubility of the drug.

TABLE 2

Effect of citric acid on the solubility of dapagliflozin in the presence of HPBCD

| Dissolving medium | Dissolved dapagliflozin (mg/mL) | Dissolving medium | Dissolved dapagliflozin (mg/mL) |
| --- | --- | --- | --- |
| HPBCD 1.0% | 4.4 | HPBCD 1.0% + 28 mg citric acid | 4.1 |
| HPBCD 2.5% | 8.6 | HPBCD 2.5% + 28 mg citric acid | 8.1 |
| HPBCD 5.0% | 14.4 | HPBCD 5.0% + 28 mg citric acid | 14.3 |

The phase "solubility isotherms" indicated that HPBCD interacts with dapagliflozin in a 1:1 molar ratio at ambient temperature.

Example 5

Preparation of a Dapagliflozin/γ-cyclodextrin Inclusion Complex 4.00 g γ-cyclodextrin (3.1 mmol, Wacker Chemie GmbH) and 1.00 g (2.44 mmol) dapagliflozin were suspended in 20 ml of distilled water. The suspension was stirred intensively at ambient temperature for six hours (protected from light). A homogenous, thick white suspension was obtained, which was filtered through a G4 sintered glass filter. The precipitate was dried at reduced pressure under $P_2O_5$ until constant weight. The obtained solid complex was ground and sieved.

Yield: 4.60 g
Residual water content: 5.4%
Dapagliflozin content: 18.55% (measured by UV spectrometry at a wavelength of 277 nm).

The X-ray powder diffraction investigations were performed on the selected dapagliflozin/γ-cyclodextrin composition by using a standard normal $CuK_{alpha}$ radiation. The reflection peaks were registered in the 2-theta angle range of 5 to 40 degrees. The solid dapagliflozin/cyclodextrin complex was prepared by using laboratory-scale waterbone technology.

FIG. 3 shows the X-ray diffractogram of the dapagliflozin/γ-cyclodextrin complex. It can be concluded that this complex has a crystalline structure.

Example 6

In Vitro Dissolution Characteristics

The dissolution studies of dapagliflozin and its γ-cyclodextrin complex were performed in simulated gastric acid (2.0 g NaCl and 80 ml of 1NHCl were diluted with distilled water to a total volume of 1.00 l).

56.1 mg of the dapagliflozin/γ-cyclodextrin complex (containing 10.4 mg of dapagliflozin) were added at 37° C. to 300 ml of the simulated gastric acid and stirred with 60 RPM.

Sampling was performed 1, 3, 5, 10, 20 and 30 min after sample addition.

As it can be seen from FIG. 4, the dissolution of dapagliflozin is considerably higher when using the dapagliflozin/γ-cyclodextrin complex as the pure dapagliflozin.

Example 7

Preparation of an Oral Dosage Form (Tablet) Containing a Dapagliflozin/HPBCD-Complex Dapagliflozin complexed with HPBCD (prepared according to Example 1) and lactose monohydrate (Tablettose 80) were blended in a Turbula® T10B at 23 rpm for 5 minutes. Microcrystalline cellulose (Avicel 112) and crospovidone (Kollidon CL) were added and the resulting mixture was blended at 23 rpm for 5 minutes. To the mixture sieved through a 1250 μm sieve colloidal silica dioxide (Aerosil) and magnesium stearate both sieved through a 1250 μm sieve, as well, were added and the resulting mixture was blended at 23 rpm for 3 minutes. After pressing the fluffy material on an eccentric press Korsch® EKO with 10 mm punches the resulting tablets were reduced to small pieces and the batch was compressed on an eccentric press Korsch® EKO with 10 mm punches to tablets, each containing

| | |
| --- | --- |
| dapagliflozin complexed with HPBCD | 109.95 mg |
| lactose monohydrate | 128.55 mg |
| microcrystalline cellulose | 40.00 mg |
| crospovidone | 8.00 mg |
| colloidal silica dioxide | 3.00 mg |
| magnesium stearate | 1.50 mg |

Example 8

Preparation of an Oral Dosage Form (Tablet) Containing a Dapagliflozin/GCD-Complex Dapagliflozin complexed with GCD (prepared according to Example 5) and lactose monohydrate (Tablettose 80) were blended in a Turbula® T10B at 23 rpm for 5 minutes. Microcrystalline cellulose (Avicel 112) and crospovidone (Kollidon CL) were added and the resulting mixture was blended at 23 rpm for 5 minutes. To the mixture sieved through a 1250 pm sieve colloidal silica dioxide (Aerosil) and magnesium stearate both sieved through a 1250 pm sieve, as well, were added and the resulting mixture was blended at 23 rpm for 3 minutes. The batch was compressed on an eccentric press Korsch® EKO with 10 mm punches to tablets, each containing

| | |
|---|---|
| dapagliflozin complexed with GCD | 135.50 mg |
| lactose monohydrate | 127.00 mg |
| microcrystalline cellulose | 40.00 mg |
| crospovidone | 8.00 mg |
| colloidal silica dioxide | 3.00 mg |
| magnesium stearate | 1.50 mg |

The invention claimed is:

1. A pharmaceutical composition comprising cyclodextrin and dapagliflozin in the form of an inclusion complex with the molar ratio of cyclodextrin to dapagliflozin being in the range from 1:1 to 2:1, wherein
cyclodextrin is selected from the group consisting of β-cyclodextrin, (2-hydroxy)propyl-β-cyclodextrin, randomly methylated-β-cyclodextrin, sulfobutylether-β-cyclodextrin, (2-hydroxy)propyl-γ-cyclodextrin and γ-cyclodextrin; and
the entire amount of dapagliflozin is entrapped intercalated into cyclodextrin and the pharmaceutical composition is essentially free of un-entrapped crystalline or amorphous dapagliflozin.

2. The pharmaceutical composition according to claim 1, wherein cyclodextrin is (2-hydroxy)propyl-β-cyclodextrin or γ-cyclodextrin.

3. The pharmaceutical composition according to claim 2, wherein the average degree of substitution of cyclodextrin is from 0.3 to 3 and the molar ratio of cyclodextrin to dapagliflozin is about 1:1.

4. The pharmaceutical composition according to claim 3, wherein each of (2-hydroxy)propyl-β-cyclodextrin and γ-cyclodextrin is in the form of a hydrate.

5. A process for producing a pharmaceutical composition according to claim 1, comprising the steps of
a) dissolving and/or dispersing cyclodextrin in a solvent;
b) adding dapagliflozin;
c) subjecting the mixture resulting from step b) to a mechanical treatment; and
d) removing the solvent from the reaction mixture by freeze-drying, spray-drying or filtration,
wherein the produced pharmaceutical composition comprises cyclodextrin and dapagliflozin in the form of an inclusion complex with the molar ratio of cyclodextrin to dapagliflozin being in the range from 1:1 to 2:1, wherein cyclodextrin is selected from the group consisting of β-cyclodextrin, (2-hydroxy)propyl-β-cyclodextrin, randomly methylated β-cyclodextrin, sulfobutylether-β-cyclodextrin, (2-hydroxy)propyl-γ-cyclodextrin and γ-cyclodextrin; and
the entire amount of dapagliflozin is entrapped intercalated into cyclodextrin and the pharmaceutical composition is essentially free of un-entrapped crystalline or amorphous dapagliflozin.

6. The process according to claim 5, wherein the cyclodextrin is (2-hydroxy)propyl-β-cyclodextrin or γ-cyclodextrin and the pharmaceutical composition is formed in the absence of excipients and/or co-solvents.

7. A pharmaceutical composition prepared by a process according to claim 5.

8. A dosage form comprising a pharmaceutical composition according to claim 1.

9. The dosage form according to claim 8, wherein the cyclodextrin is in the form of a hydrate.

10. The dosage form according to claim 8, wherein the dosage form is adapted to be administered orally or intravenously.

11. A method of purification of dapagliflozin, comprising the steps of
a) dissolving or dispersing cyclodextrin in a solvent;
b) adding crude dapagliflozin;
c) separating the complexed dapagliflozin from non-complexed residues by filtration,
wherein cyclodextrin and dapagliflozin form an inclusion complex with the molar ratio of cyclodextrin to dapagliflozin being in the range from 1:1 to 2:1, and wherein cyclodextrin is selected from the group consisting of β-cyclodextrin,(2-hydroxy)propyl-β-cyclodextrin, randomly methylated γ-cyclodextrin, sulfobutylethery-cyclodextrin, (2-hydroxy)propyl-γ-cyclodextrin and γ-cyclodextrin; and the entire amount of dapagliflozin is entrapped intercalated into cyclodextrin and the pharmaceutical composition is essentially free of un-entrapped crystalline or amorphous dapagliflozin.

12. A dosage form comprising cyclodextrin and dapagliflozin in the form of an inclusion complex with the molar ratio of cyclodextrin to dapagliflozin being in the range from 1:1 to 2:1, characterized in that on introduction to water said dosage form is capable of forming a solution comprised of not less than 5 mg dapagliflozin per ml water, wherein cyclodextrin is selected from the group consisting of β-cyclodextrin, (2-hydroxy)propyl-γ-cyclodextrin, randomly methylated β-cyclodextrin, sulfobutylether-β-cyclodextrin, (2-hydroxy)propyl-γ-cyclodextrin and γ-cyclodextrin; and the entire amount of dapagliflozin is entrapped intercalated into cyclodextrin and the pharmaceutical composition is essentially free of un-entrapped crystalline or amorphous dapagliflozin.

13. The dosage form according to claim 12, wherein cyclodextrin is (2-hydroxy)propyl-β-cyclodextrin or γ-cyclodextrin.

14. The dosage form according to claim 9, wherein the dosage form is adapted to be administered orally or intravenously.

15. The pharmaceutical composition according to claim 4, wherein the inclusion complex comprises (2-hydroxy)propyl-β-cyclodextrin and dapagliflozin and is in non-crystalline form, wherein each molecule of (2-hydroxy)propyl-β-cyclodextrin comprises between 12 and 14 molecules of water.

16. The pharmaceutical composition according to claim 4, wherein inclusion complex comprises γ-cyclodextrin and dapagliflozin and is in crystalline form, wherein each molecule of γ-cyclodextrin comprises between 12 and 14 molecules of water.

17. The dosage form according to claim 12, wherein the inclusion complex comprises (2-hydroxy)propyl-β-cyclodextrin and dapagliflozin and is in non-crystalline form, wherein (2-hydroxy)propylβ-cyclodextrin is in the form of a hydrate and each molecule of (2-hydroxy)propyl-β-cyclodextrin comprises between 12 and 14 molecules of water.

18. The dosage form according to claim 12, wherein inclusion complex comprises γ-cyclodextrin and dapagliflozin and is in crystalline form whereinγ-cyclodextrin is in the form of a hydrate and each molecule of γ-cyclodextrin comprises between 12 and 14 molecules of water.

* * * * *